United States Patent
Moore et al.

(10) Patent No.: US 8,440,969 B2
(45) Date of Patent: May 14, 2013

(54) METHOD AND APPARATUS FOR ACQUIRING SIMULTANEOUS AND OVERLAPPING OPTICAL AND CHARGED PARTICLE BEAM IMAGES

(75) Inventors: Thomas M. Moore, Dallas, TX (US); Cheryl Hartfield, Plano, TX (US); Gregory A. Magel, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 156 days.

(21) Appl. No.: 13/196,240

(22) Filed: Aug. 2, 2011

(65) Prior Publication Data

US 2012/0025075 A1 Feb. 2, 2012

Related U.S. Application Data

(60) Provisional application No. 61/369,864, filed on Aug. 2, 2010.

(51) Int. Cl.
*H01J 37/22* (2006.01)
*H01J 37/26* (2006.01)

(52) U.S. Cl.
USPC ............................... 250/307; 250/311

(58) Field of Classification Search ........... 250/306–311
See application file for complete search history.

(56) References Cited

U.S. PATENT DOCUMENTS

| | | | |
|---|---|---|---|
| 5,780,853 A | 7/1998 | Mori et al. | |
| 7,045,791 B2 | 5/2006 | Benas-Sayag et al. | |
| 7,297,948 B2* | 11/2007 | Benas-Sayag et al. | 250/306 |
| 7,351,966 B1 | 4/2008 | Marchman et al. | |
| 7,671,333 B2 | 3/2010 | Agronskaja et al. | |
| 8,097,849 B2* | 1/2012 | Ohtomo et al. | 250/310 |
| 2005/0168730 A1 | 8/2005 | Sakai et al. | |
| 2007/0284526 A1 | 12/2007 | Nara et al. | |
| 2008/0029699 A1* | 2/2008 | Kaneoka et al. | 250/307 |
| 2008/0073524 A1 | 3/2008 | Nishiyama et al. | |
| 2008/0073527 A1 | 3/2008 | Nakazawa et al. | |
| 2008/0273193 A1 | 11/2008 | Nishiyama et al. | |
| 2008/0296499 A1* | 12/2008 | Faber | 250/311 |
| 2009/0242762 A1 | 10/2009 | Nishiyama et al. | |
| 2009/0274359 A1 | 11/2009 | Nakazawa et al. | |

FOREIGN PATENT DOCUMENTS

| | | |
|---|---|---|
| JP | 2003016988 A | 1/2003 |
| WO | 93/18525 | 9/1993 |

OTHER PUBLICATIONS

International Searching Authority, International Application No. PCT/US2011/046247, International Search Report and the Written Opinion Mar. 12, 2012.
New Scanning Electron Microscope Capable of Observing Cells in Solution;—High Resolution Atmospheric SEM Imaging of Cells in the Same Area of View as Optical Microscopy—; Dec. 8, 2008, National Institute of Advanced Industrial Science and Technology, JEOL Ltd.
Masahiro Nakajima, Nano-injection System based on Nanorobotic Manipulations inside Hybrid Microscope, 2010 IEEE Nanotechnology Materials and Devices Conference, Joint 1st IEEE International Symposium on Energy, Environment, Safety and Security, Oct. 12-15, 2010, monterey, California, USA.
Takaaki Kanemaru, A fluorescence scanning electron microscope, Ultramicroscopy 109 (2009) 344-349.
Alexandra V. Agronskaia, Integrated fluorescence and transmission electron microscopy, Journal of Structural Biology 164 (2008) 183-189.
The International Bureau of WIPO, International Application No. PCT/US2011/046247, International Preliminary Report on Patentability, Feb. 5, 2013.

* cited by examiner

*Primary Examiner* — Robert Kim
*Assistant Examiner* — David E Smith
(74) *Attorney, Agent, or Firm* — John A. Thomas

(57) ABSTRACT

This disclosure relates to a method and apparatus for producing multiple pixel-by-pixel simultaneous and overlapping images of a sample in a microscope with multiple imaging beams. A scanning electron microscope, a focused ion-beam microscope, or a microscope having both beams, also has an optical microscope. A region of interest on a sample is scanned by both charged-particle and optical beams, either by moving the sample beneath the beams by use of a mechanical stage, or by synchronized scanning of the stationary sample by the imaging beams, or by independently scanning the sample with the imaging beams and recording imaging signals so as to form pixel-by-pixel simultaneous and overlapping images.

30 Claims, 13 Drawing Sheets

METHOD AND APPARATUS FOR ACQUIRING SIMULTANEOUS AND OVERLAPPING OPTICAL AND CHARGED PARTICLE BEAM IMAGES

CLAIM FOR PRIORITY

This application claims the benefit of U.S. Provisional Application, Ser. No. 61/369,864, filed Aug. 2, 2010, and titled "Method For Acquiring Simultaneous And Overlapping Optical And Charged Particle Beam Images," which is incorporated by reference in its entirety into the present application.

BACKGROUND

1. Technical Field

This disclosure relates to specimen-observation methods in a multi-beam microscope comprising both a charged-particle beam and an optical microscope. Examples of charged-particle beam microscopes include focused-ion beam microscopes (FIB), or scanning-electron microscopes (SEM) or combinations of the same (for example, a combined SEM/FIB), or a transmission electron microscope (TEM). This disclosure relates, in particular, to methods for generating optical and charged particle images from the same field of view while the sample is contained within a charged-particle beam microscope chamber.

2. Background

Life science researchers have traditionally relied on optical microscopy to examine tissue and cell samples and on TEM when needing to resolve subcellular details. Recent hardware improvements now enable SEMs to offer TEM-like images with resolution approximately 3-5 nm. Because of their larger chambers and reduced cost compared to TEM, SEMs offer an ideal platform for integration of combined imaging modalities. The ability to simultaneously image the same area of a sample with both electrons and photons enables real-time correlated imaging, avoids the need to generate entire image maps over large areas with optical microscopy, reduces the chance of sample damage during transfer between different microscopes, and saves analysis time.

Multi-beam charged-particle microscopes are commercially available. These instruments have a vacuum chamber that contains two or more charged particle imaging beams. The charged particle beams can include, but are not limited to, electron and ion beams such as in a scanning electron microscope (SEM), a focused ion beam microscope (FIB), and an SEM/FIB (also called a dual beam SEM/FIB or FIB/SEM) which has both a scanned ion beam and a scanned electron beam. FIBs typically use a gallium liquid metal ion source, but recent advances in imaging technology (such as the Orion He ion microscope (HIM) manufactured by Carl Zeiss Nano Technology Systems GmbH, Oberkochen, Germany) make possible the use of other ion beams for imaging purposes. Unless otherwise stated, a reference to imaging by an SEM or a charged-particle beam microscope should be taken to also refer to imaging by multi-beam ion and electron charged-particle beams, including ions of a variety of species such as the HIM or those delivered with a mass-filtered column technology, which offers sources based on Si, Cr, Fe, Co, Ni, Ge, In, Sn, Au, Mn, Pb, etc.

Since the images produced by a charged particle beam microscope and the optical microscope have widely varying resolutions and are formed based on different signals and contrast mechanisms, the image appearances and qualities are exceedingly different from each other. Consequently, it has been difficult and time-consuming to retrieve the observation field-of-view of the electron microscope on the basis of the specimen image acquired using the optical microscope. What is needed is a way to coordinate the images produced by the charged-particle beam and the optical illumination.

DRAWINGS

DESCRIPTION

Figure 1:
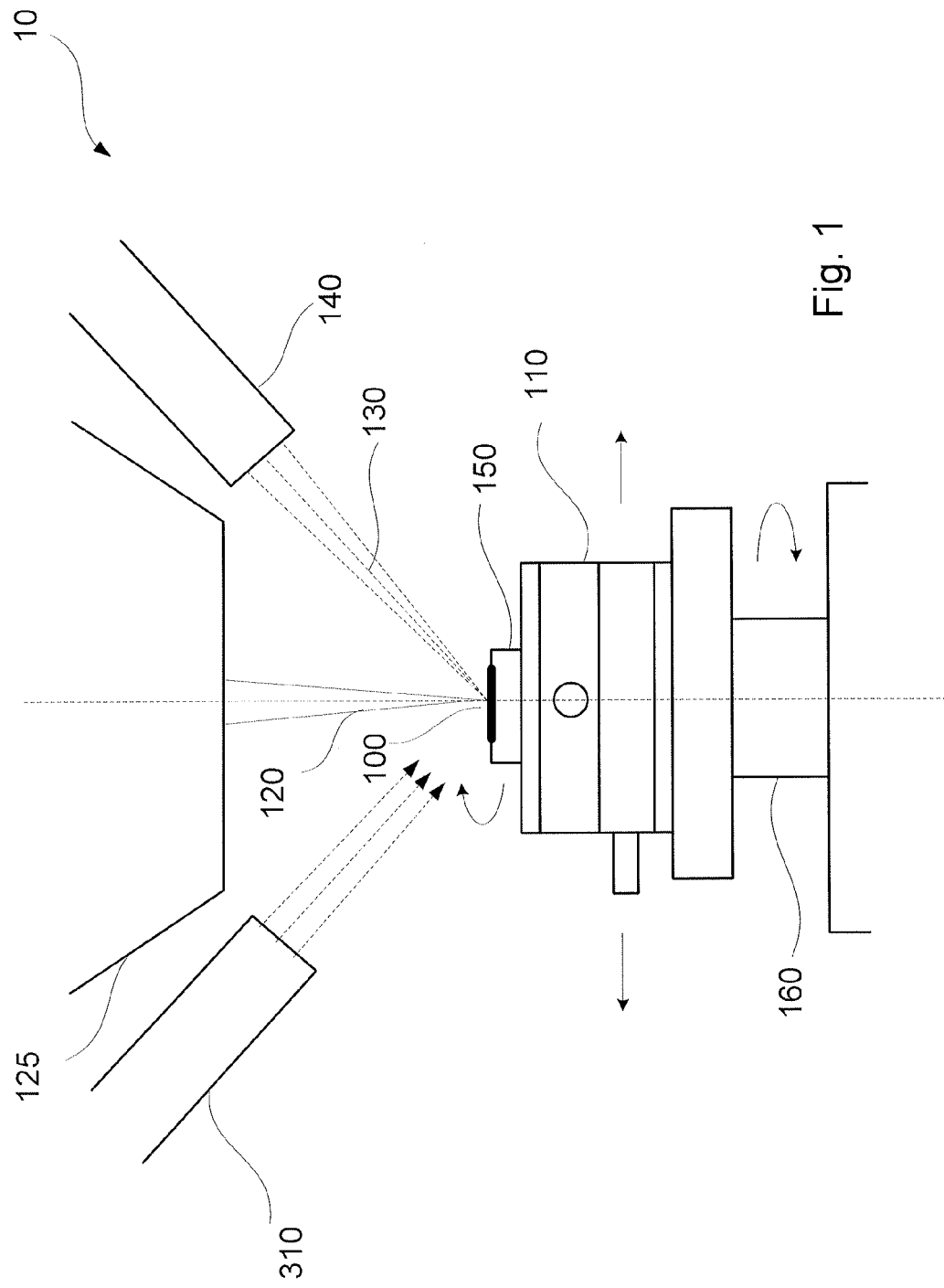
FIG. 1 is a schematic diagram showing the interior of a microscope according to an embodiment.
Figure 2:
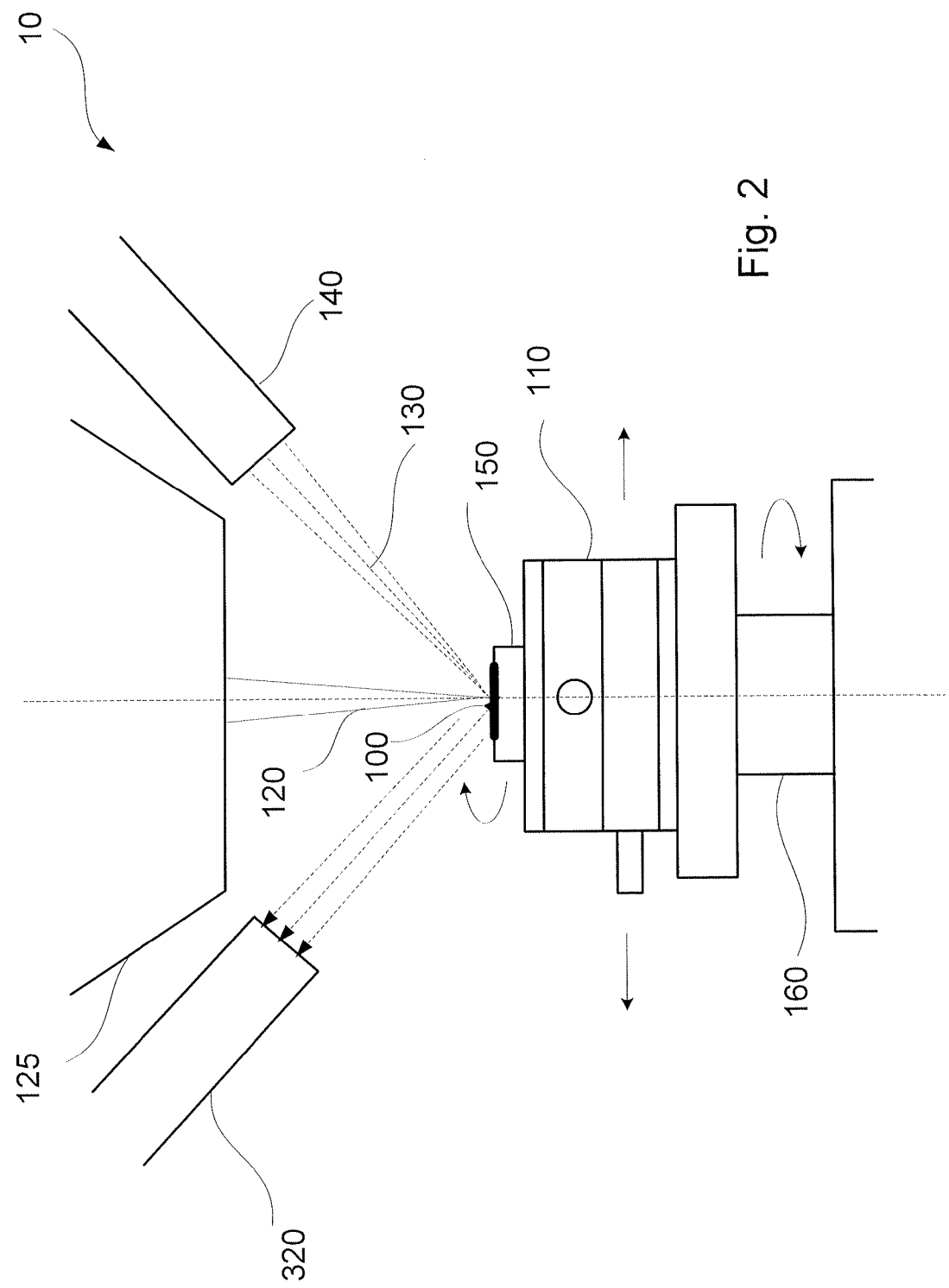
FIG. 2 is a schematic diagram showing the interior of a microscope according to another embodiment.
Figure 3:
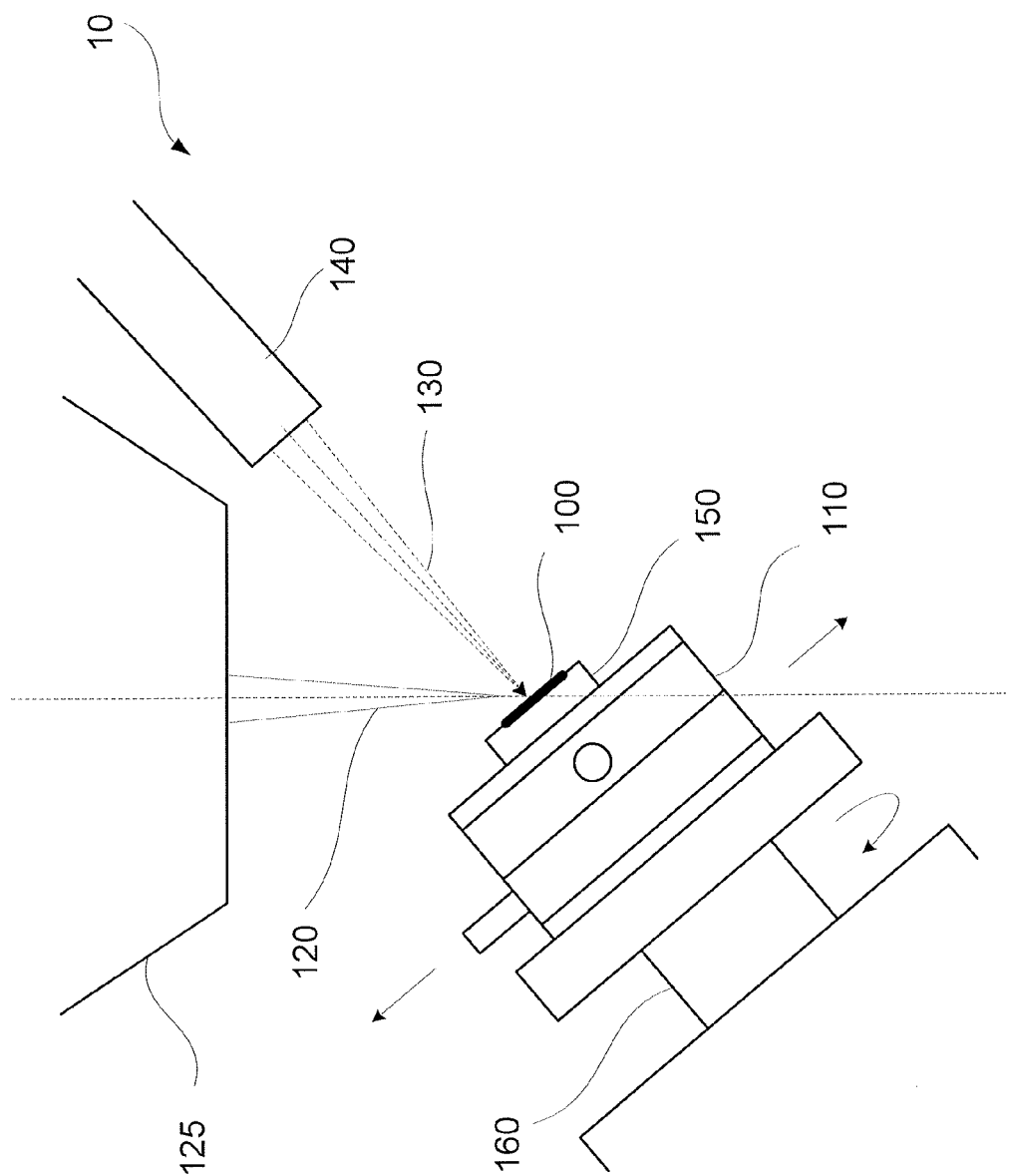
FIG. 3 is a schematic diagram showing the interior of a microscope according to another embodiment.

As shown in FIGS. 1-3, a sample 100 to be imaged is mounted in the vacuum chamber of a multi-beam microscope 10. In some embodiments, the sample 100 is mounted on a high-resolution mechanical scanning stage 110 with positioning accuracy and reproducibility commensurate with the resolution requirements of the desired images. A suitable scanning stage 110 is an X-Y stacked pair of model PInano™ Nanopositioning System available from PI (Physik Instrumente) GmbH & Co. Z-axis stage movement perpendicular to the X and Y orthogonal scan plane can be included beneath the X and Y scan elements to enable fine focus adjustments. An optical microscope 140, such as the Omniprobe Opto-Probe™ system, manufactured by Omniprobe, Inc., can be positioned in an accessory port having an oblique angle of incidence with X and Y orthogonal scan plane of the mechanical scanning stage 110. Typically, these accessory ports are located with roughly a 45-degree angle of incidence relative to the horizontal plane (the X-Y orthogonal scan plane). With this orientation of the optical beam 130 and electron beam 120, pixel-by-pixel simultaneous and overlapping images (explained below) can be formed using the focused electron beam 120 and the focused optical beam 130 while scanning the mechanical scanning stage 110.

Optical imaging may be performed by optical microscope 140 using any of a large number of methods known in the art, including, but not limited to, reflected or transmitted light, polarized light, fluorescence, and nonlinear optical methods, and using either wide-field or scanning methods. In some embodiments, scanning methods for optical imaging are used, in which optical microscope 140 is used to image a single optical spot on the sample at a time. The light that is gathered from the sample can be generated within the sample, e.g. by fluorescence or cathodoluminescence, in response to excitation by light delivered to the sample by optical beam 130 (or a separate light source) or by electrons delivered to the sample by electron beam 120. More commonly, light that has been delivered either by optical microscope 140 along optical beam 130, or from a separate light source 310 as shown in FIG. 1, is reflected or transmitted by the sample to optical microscope 140 or to a separate optical detector 320 as shown in FIG. 2. In any of these embodiments, the optical spot that is being imaged at any given point in time is defined by the position and focus of optical beam 130 on sample 100.

An embodiment using the mechanical scanning stage 110 is shown in FIGS. 1 through 3. This stage 110 may be mounted in the multi-beam microscope at a variety of angular relationships to the imaging beams. For example, if an SEM is used as the base for the multi-beam microscope, the electron beam column 125 is typically positioned vertically so that the electron beam 120 impinges the sample 100 in a vertical direction. The scan plane of the mechanical scanning stage 110 can be oriented to be perpendicular to this electron beam 120 as shown in FIGS. 1-2, or perpendicular to the optical beam 130 as shown in FIG. 3. Since depth of focus of the electron beam is typically greater than the depth of focus of the optical beam, the tilted configuration of the mechanical scanning stage 110, shown in FIG. 3, relative to the electron beam 120, is preferred.

In the configuration shown in FIG. 1, a secondary light source 310 illuminates the sample at the appropriate angle for reflection of the incident light into the optical microscope 140. In the configuration shown in FIG. 2, the focused incident light 130 is introduced by the optical microscope, and a secondary light detector 320 detects the reflected light. In the configuration shown in FIG. 3, the incident light 130 is introduced, and the reflected light is detected by the optical microscope 140.

In this disclosure, the charged particle beam may be referred to as the charged particle beam, the electron beam or the ion beam, but in all cases this refers to one or more charged particle beams, each focused at the coincidence point.

Figure 4:
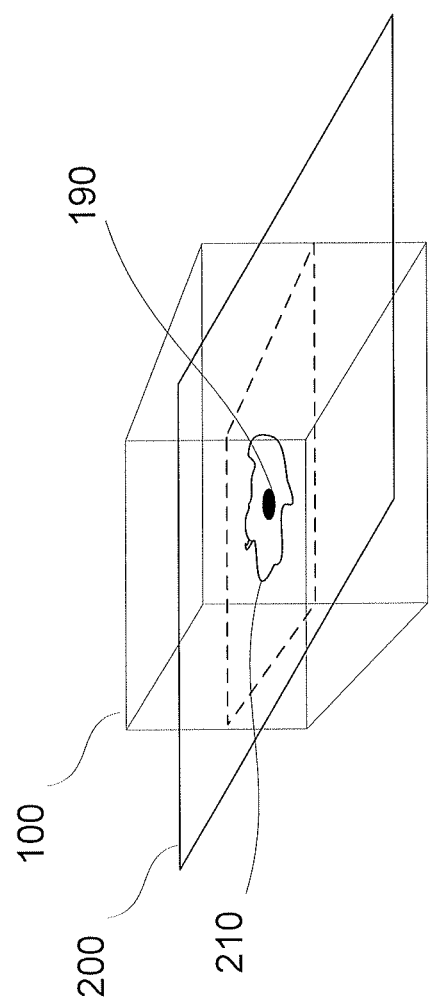
FIG. 4 is a schematic diagram of a sample geometry according to an embodiment.

FIG. 4 shows a schematic representation of the intersection of the object plane 200 with the sample 100. The region of interest 210 is shown as a non-rectangular shape lying on the object plane 200. The coincidence point 190 is shown to be located, for example, in the object plane 200 and within the region of interest 210.

Figure 5:
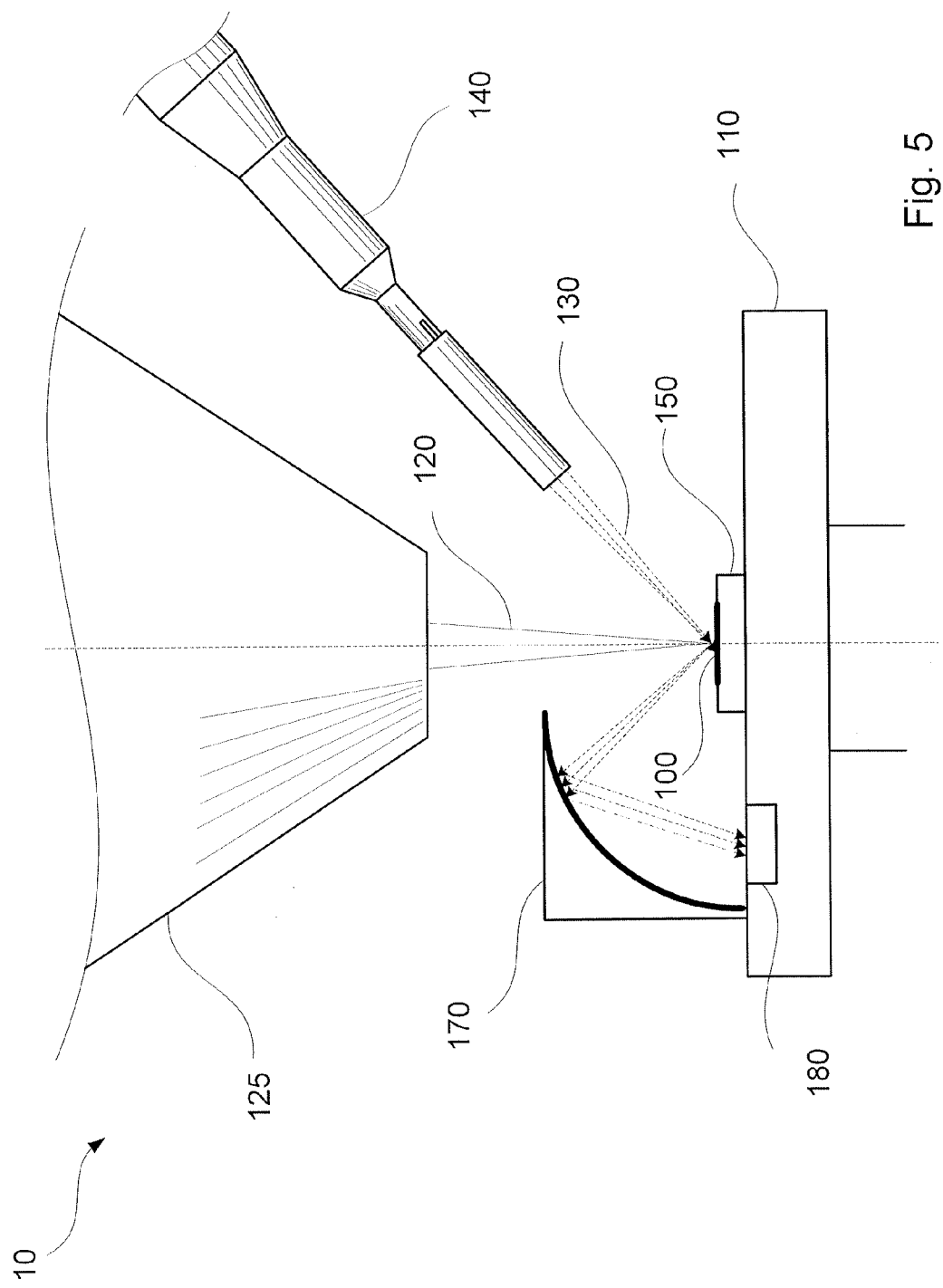
FIG. 5 is a schematic diagram showing the interior of a microscope according to an embodiment.

As shown in FIG. 5, an alternative arrangement enables reflected light imaging during mechanical scanning, where the optical imaging beam 130 is at an oblique angle of incidence with respect to the sample 100, a reflector 170 and a secondary optical detector 180 can be used to collect the reflected light from the optical beam 130. This system has a light reflector 170 positioned on the opposite side of the sample 100 relative to the position of the optical imaging beam 130, and a light detector 180 embedded in the surface of the stage 110. The reflector 170 can be planar, spherical, ellipsoidal or any other appropriate shape depending on the position of the mirror and the light detector 180. Alternatively, the reflector 170 can be replaced with a solid-state light detector or detector array.

Figure 6:
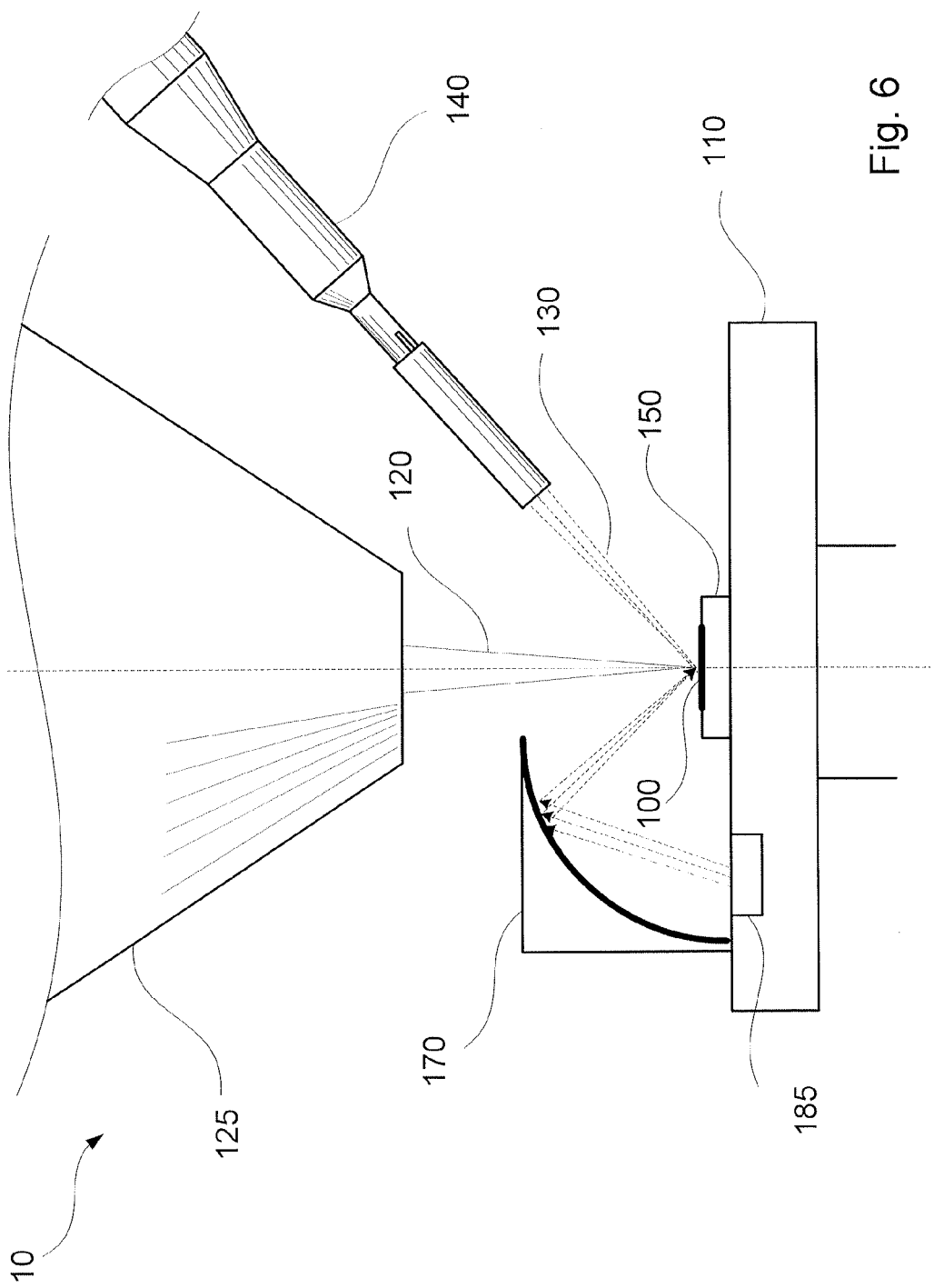
FIG. 6 is a schematic diagram showing the interior of a microscope according to another embodiment.

Alternatively, as shown in FIG. 6, the incident light can be generated by a light source, such as an LED, embedded in the mechanical scanning stage 110 and this incident light can be reflected from a suitable optical reflector 170 and projected onto the sample 110 at the appropriate angle to reflect into the optical imaging microscope 140.

Images in a set of two or more images are defined as "pixel-by-pixel simultaneous and overlapping images" when the information recorded in a given pixel, for each pixel of the entire image, was acquired at the same time simultaneous within one pixel duration) and from the same location within the same sample pixel area 240 on (or in) the sample 100. For example, pixel-by-pixel simultaneous and overlapping images can be acquired by scanning the sample 100 with the mechanical scanning stage 110 while operating the imaging beams 120, 130 in the stationary spot mode with all beams spots focused at the coincidence point 190. The coincidence point 190 is contained in the object plane on (or in) the sample 100.

An "image set" is one or more images formed from one or more detectors, with the same image magnification and from the same region of interest 210 on the sample 100. Each detector senses a signal generated by the interaction of one imaging beam with the sample 100.

The "coincidence point" 190, shown schematically in FIG. 4, is a single location in space where the foci of both of the imaging beams 120, 130 intersect.

The "sample pixel area" 240 is the two dimensional physical area on (or in) the sample 100 which corresponds to one pixel area in the corresponding image or images. Both imaging beams have a focus, and a depth of focus. The electron beam spot 220 and the optical beam spot 230 are depicted (not to scale in FIGS. 11 and 12. Since the minimum size of the optical spot 230 is larger than the minimum achievable electron beam spot 220, the sample pixel area 240 is typically determined by the size of the optical spot 230.

The "sample pixel duration" is the amount of time during which each sample pixel area 240 is exposed to the imaging beam or beams during a single image scan.

As shown in FIG. 4, the "object plane" 200 is a plane containing the coincidence point 190, parallel to the plane of movement of the mechanical scanning stage 110, and passing either through the sample 100 (transmission imaging), or along the surface of the sample 100 (surface imaging), from which area the image is desired. The region of interest 210 lies within the object plane 200. The region of interest 210 is typically square or rectangular, but may be any two dimensional shape.

Images are "independent simultaneous and overlapping images" when the time periods during which these images are acquired are at least partially concurrent and these images are at least partially overlapping in space.

Pixel-by-pixel simultaneous and overlapping images are obtained at the same magnification from the same region of interest 210 (ROI) regardless of whether the images have the same or different pixel densities and image resolutions. In most cases, the images in an image set will have the same pixel density. However, using the example of an SEM image and an optical image that are in coincidence over the same region, the SEM image may have more pixels for the same image magnification to take advantage of the significantly smaller spot size of the electron beam 120.

Note that in order to isolate similar detector signals produced by different imaging beams 120, 130, the exposure of the sample 100 to the different imaging beams 120, 130, as well as the detection of the resulting signals, may be gated in time, but accomplished during one sample pixel duration and while the focused imaging spots expose one sample pixel area 240. For example, secondary electrons generated by an ion beam and an electron beam 120 may be differentiated from each other by gating the ion and electron beam 120, and the secondary electron signal detection, in time. Similarly, if secondary electrons are generated during light exposure (photoelectric effect), the light beam and the electron beam 120 can be gated in time, as well as the associated detected signals, to prevent the laser illumination from producing a high background of secondary electron signal in the e-beam induced secondary electron image (SEM image).

Software or hardware correction for mechanical drift within the microscope may be implemented as is known in the art.

Multispectral imaging here means acquiring a spectrum of a radiation triggered by the laser illumination at each pixel in a sample pixel area and using the acquired spectra to produce images of specific properties of the spectra. A spectrum can be acquired to show any one of several types of information. For example, spectra can be formed of the fluorescent optical emission (intensity vs. wavelength) from the sample 100 during laser spot illumination, or of secondary electron energy (intensity vs. energy) during electron beam 120 irradiation. Images generated from these spectra can be formed in real time, or as part of a post-processing operation.

A suitable alignment mark can be used to focus all of the imaging beams to a common point, the coincidence point 190. The alignment mark preferably has a physical feature that is detectable by all imaging beams 120, 130, and may be, for example, a physical "X" pattern machined into the surface of the sample holder 150 in the same plane as the surface of the sample. Similarly, if the imaging beams 120, 130 include an ion beam, an electron beam 120 and an optical beam 130, an alignment sample, or alignment mark, would be suitable if it had a physical feature that was detectable and resolvable in images produced by the ion beam, the electron beam and the optical beam. The alignment mark can be incorporated into the surface of the sample 100 or incorporated into the alignment sample positioned immediately adjacent to the sample, so that the surface of the alignment sample, or alignment mark, and the surface of the sample lie in the same plane.

First Embodiment

Scanning with a Mechanical Sample Stage

Figure 7:
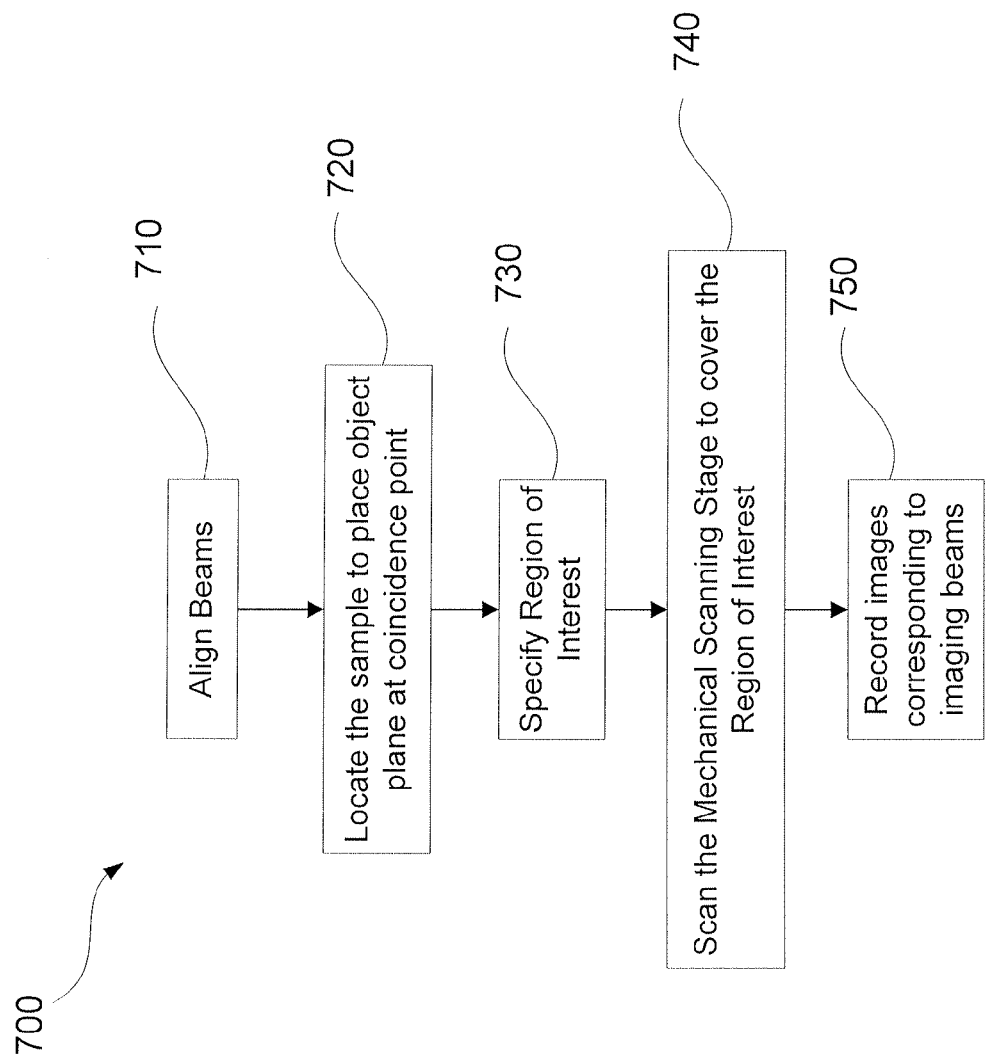
FIG. 7 is a flow chart showing a method for obtaining simultaneous and overlapping images according to one embodiment.

Referring now to FIG. 7, a flow chart of a process 700 for acquiring simultaneous and overlapping charged particle and optical images using a mechanical stage to scan the sample is shown. A sample 100 is assumed to have been provided for imaging within the multi-beam microscope in the conventional way, for example by mounting on the mechanical stage through a door or loadlock and evacuating the chamber for charged particle beam imaging. First, in step 710, the optical beam 130 or optical viewing axis and the charged particle beam or beams 120 are aligned so that their focal regions overlap at a coincidence point 190, as shown in FIG. 4. This alignment can be performed by imaging an identifiable feature that can be imaged by both beams (or all beams if there are more than two, such as in a dual-beam FIB/SEM with additional optical imaging). Such an identifiable feature may be found somewhere on sample 100 to be analyzed, or by using a separate alignment sample with known features, or by a fiducial mark provided on the sample holder 150, or elsewhere, such as on the mechanical scanning stage 110 itself, preferably close to the area of the sample to be imaged so as to maintain beam positioning accuracy and focus properties when the imaging beams are directed onto the sample.

Then, in step 720, the sample 100 is located so as to place a desired object plane 200 at the coincidence point of the charged particle beams. In other words, the coincidence point 190 is to be positioned within the desired object plane 200. Tilting and rotation functions of the sample stage or translation mechanisms built into the microscope can be used to determine the orientation as well as the position of object plane 200. The object plane 200 will commonly be at or near the plane of the upper surface (towards the charged particle beam incident direction) of the sample. But in the case when imaging in transmission mode for either the charged particle or optical beam, or when imaging a sample with significant non-planar topography, or when imaging of a plane within some depth inside the sample, such as within an optically transparent sample, or when the penetration depth of the charged particle beam can be used to perform an analysis of a region buried below the sample surface, the object plane 200, as described before, may lie within the sample, or below the top surface of the sample, or below the highest points on the sample.

A region of interest 210 is then specified or selected for scanning in step 730. If sample geometry is known and the sample has already been mapped by imaging outside the microscope, it may be possible to simply enter coordinates (together with appropriate transformations) into a controller (not shown) for the scanning stage 110. However, a common mode of operation will be to perform a survey or lower-magnification imaging using either the charged particle beam or the optical imaging capabilities of multi-beam microscope 10 to determine the shape, dimensions, and/or extents of region of interest 210. These extents need not be square or rectangular or indeed any regular shape, although rectangular is the most common shape of a scanned area in imaging. Then in step 740, the mechanical scanning stage 110 is controlled to move the sample such that the coincidence point is scanned to cover the specified region of interest 210. Any suitable scanning pattern shape or sequence can be used as is known in the art.

Using exemplary data collection timing sequences such as those shown and described later in connection with FIG. 13 while the stage 110 is being scanned, image data from both imaging beams is collected in step 750, and recorded in the form of images that can be displayed while the stage 110 is being scanned, or saved for later display. Because the beams maintain their alignment during the scanning, it will be appreciated that the images are acquired both simultaneously and with excellent registration or overlap. Registration is particularly good for samples that have little topography and for features that lie within object plane 200. The recorded images acquired in step 750 can be compared side-by-side, or overlaid using techniques already discussed to form composite images that are for example color-coded to show sample areas with particular properties that are of interest, such as areas that are visible in one modality but not the other.

For example, if some sample areas are optically fluorescent but indistinguishable by the charged particle beam imaging modality, a composite image can be made that uses false color to highlight the optically fluorescent areas within a grey-scale image. If one or both imaging modalities can be used to acquire a spectrum such as an optical fluorescence spectrum, or an energy spectrum of secondary electrons, e.g. using energy dispersive spectroscopy (EDS), then the step 750 of recording an image can be generalized to include recording a spectrum stimulated by one or both of the beams at some or all of the pixels of the image. This type of imaging is referred to as multispectral or hyperspectral imaging. It is equivalent to recording multiple images, one for each value of the spectral parameter such as optical wavelength that is measured at each pixel where spectral data has been acquired. Spectral selection may be applied in real time or an "image stack" can be stored and processed e.g. with Boolean or other mathematical functions to generate new images, as is known in the art.

Scanning the sample 100 using a mechanical stage 110 has the advantage of ensuring good synchronism and overlay between images gathered by both the charged particle and optical beam imaging modalities. Image acquisition times can be longer than in some of the other embodiments using beam scanning, which can be faster and can achieve shorter pixel-to-pixel motion times and/or line-to-line times.

Second Embodiment

Scanning with Synchronized Imaging Beams

Figure 8:
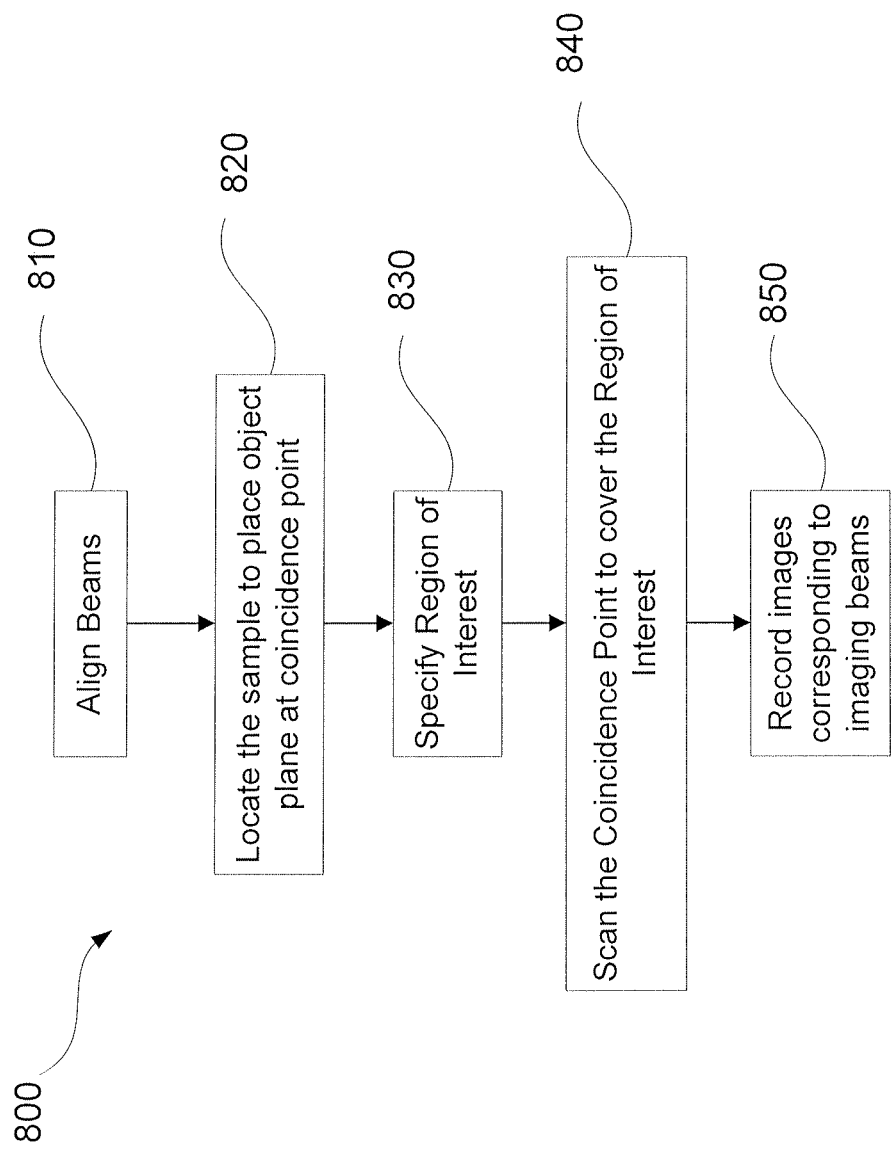
FIG. 8 is a flow chart showing a method for obtaining simultaneous and overlapping images according to a second embodiment.

Referring now to FIG. 8, a process flow 800 for acquiring simultaneous and overlapping charged particle and optical images using coordinated scanning of charged particle and optical beams to scan the sample is shown. As in the first embodiment, a sample 100 is provided to be imaged within a multi-beam microscope 10. Again, as a first step 810, the optical beam 130 or optical viewing axis and the charged particle beam or beams 120 are aligned so that their focal regions overlap at a coincidence point 190. This alignment can be performed using one of the same techniques discussed earlier, such as using fiducial marks, or by simply finding a recognizable feature on the sample to image with both beams.

The sample 100 position and height are adjusted in step 820 to locate the sample 100 and to place an object plane 200 so that it contains the coincidence point and is oriented and positioned as desired to acquire the desired images. Once the object plane 200 is defined within the sample, in step 830 a region of interest 210 is specified within which to scan. The charged particle beam and optical viewing axis or beam are then scanned in synchronism and coordination in step 840 so as to maintain the coincidence point 190 within the object plane 200, while moving the coincidence point 190 in a scanning pattern that includes the region of interest 210. Again, suitable scanning patterns are known in the art, and are performed so as to cover the region of interest sufficiently completely to generate the desired images. Note that the scanning pattern may extend beyond the region of interest 210. It may be advantageous to dynamically adjust the focus of one or both beams such that the focal spot size remains small throughout the scan pattern, i.e., to keep the coincidence point 190 lying close enough to stay within the object plane 200. Finally, in step 850, images corresponding to both imaging beams 120 and 130 are recorded.

It will be appreciated that by using this technique, simultaneous and overlapping images are again acquired from both imaging beams with good registration. An advantage of this embodiment is that more rapid scanning may be achieved by moving the beams electronically (in the case of charged particle beams) or optically (e.g. using galvanometer scanners) than by moving the more massive stage 110 and sample 100. Images acquired by this technique can be analyzed, overlaid, and annotated using conventional techniques as in the other embodiments.

Third Embodiment

Independent Scanning of Optical and Charged Particle Beams

Figure 9:
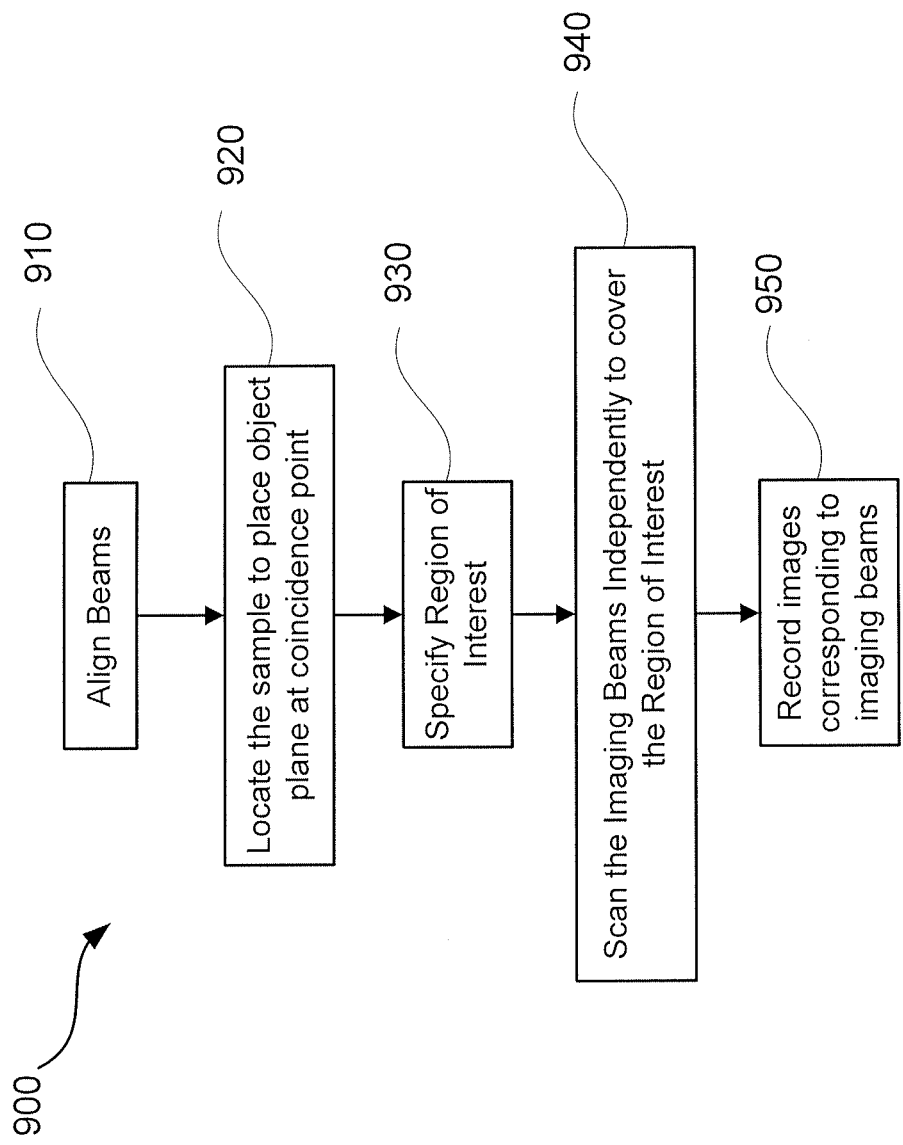
FIG. 9 is a flow chart showing a method for obtaining simultaneous and overlapping images according to a third embodiment.

Referring now to FIG. 9, a process flow 900 is provided for acquiring simultaneous and at least partially overlapping images. In this embodiment, both optical and charged particle images are obtained, like in the second embodiment, by scanning the beams instead of the sample stage. But in this case, the beams are not synchronized so as to maintain their foci together at a coincidence point that lies within the object plane at all times. Instead, the focus of the charged particle beam and the focus of the optical beam (or optical microscope) are both separately and independently maintained within the object plane during the scanning, but the two foci may be located at two different points within independent scan patterns covering the region of interest 210 at any given moment.

As before, a sample 100 is provided and an initial alignment of the beams is performed in step 910. This step is to focus the beams at the desired object plane. Then, as before, in step 920 the sample 100 is located such that the object plane lies in the desired position within the sample 100 volume or on or near the sample 100 surface. A region of interest within the object plane is specified in step 930. In step 940, scanning is performed independently. The two beams may or may not simultaneously address a particular point of the region of interest 210 within a single pixel time, but may simultaneously acquire a line or an area of an overlapping image within less than a complete frame time, defined as the time to acquire both images from both modalities within the entire region of interest 210. Since the charged particle and optical beams are scanned independently, they may use different scan patterns of different shapes or sizes, or have different timing parameters such as line times, or even use a combination of different scan patterns such as rasters with and without flyback, spirals, or other patterns. Note that either or both of the scan patterns may extend beyond the region of interest 210. During a frame time, signals from one or more detectors are collected to generate both images, which are recorded in step 950 for display, comparison, or analysis.

Fourth Embodiment

Mechanical or Optical Line Scanning, Electronic Subpixel Scanning

Figure 10:
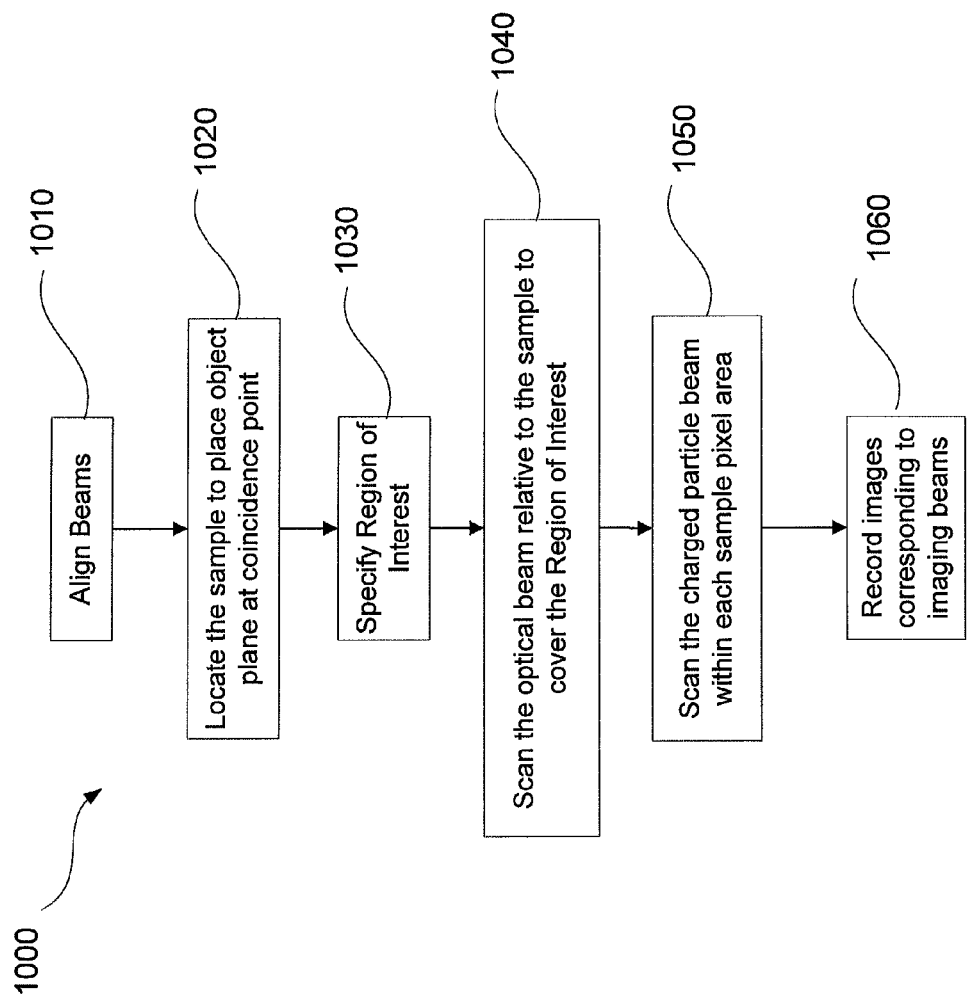
FIG. 10 is a flow chart showing a method for obtaining simultaneous and overlapping images according to a fourth embodiment.

Referring now to FIG. 10, a process flow 1000 for making use of the higher resolution available from charged particle beams is provided, while obtaining simultaneous and overlapping images from at least two modalities. Scanning from pixel to pixel can be performed using either mechanical scanning of the sample using a mechanical scanning stage, or using optical scanning. Subpixel scanning of a charged particle beam within each optical pixel is performed either for obtaining improved data/signal quality such as for better averaging, or to allow creation of a higher resolution charged particle beam image that is registered on a pixel by pixel basis with the optical image (where sample pixel area or, equivalently, pixel size is determined by the optical resolution).

As in the other embodiments, the process begins with a step 1010 of aligning the beams so as to place their foci in coincidence near a desired point in space near, on, or within a sample. In step 1020, the sample is located so as to place an object plane that is to be scanned in such a way that it contains the coincidence point. Also as before, step 1030 comprises specifying a region of interest within the object plane over which an image is to be obtained.

In step 1040, the optical beam is scanned relative to the sample. This can be accomplished in either of two ways: the optical beam can be fixed as in the first embodiment, and the sample scanned using a mechanical scanning stage; or, the sample can be stationary and the optical beam can be scanned using an optical scanning method. Depending on the relative scanning speeds, a dwell time may be used so that the optical beam stops or pauses within one sample pixel area before moving to the next pixel. As discussed later in connection with FIG. 13, the total time including the optical dwell time and the pixel-to-pixel motion time is defined to be the pixel-to-pixel scan time. During an optical dwell time, the charged particle beam can be moved within a sample pixel area in a scanning or other fashion such as dithering. Such a motion 1050 of the charged particle beam allows it to sample a larger area than if it were simply stopped at a point such as the center of the pixel for the duration of the optical dwell time. This can result in better averaging of properties to be imaged by the charged particle beam.

Alternatively, since the spot size of a charged particle beam such as an electron beam can be considerably smaller than that of the optical beam (i.e. the sample pixel area), scanning of the charged particle beam 1050 can be performed independently to acquire an image within one or more sample pixel areas. If such an image is acquired within many sample pixel areas, then an array of these images, properly stitched, can be assembled into a charged particle beam "super-image" that is registered with and overlaps the optical image and has much higher resolution. It will be appreciated that the charged particle beam image is simultaneously acquired and also is a higher-resolution image of an overlapping area of the optical image obtained by scanning the sample or the optical beam. Both images are recorded, and stored and/or displayed in step 1060.

Figure 11:
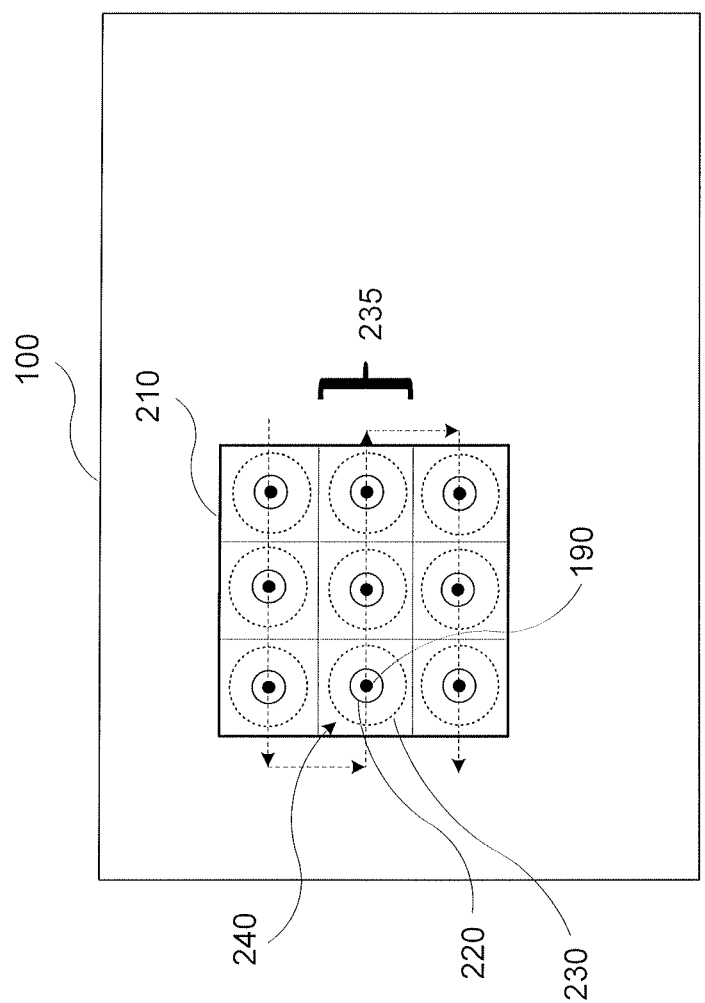
FIG. 11 is a schematic diagram showing a scanning pattern including spot sizes and pixels according to an embodiment.

FIG. 11 is a two-dimensional schematic view of an object plane within sample 100 showing a scanning pattern that represents both the first (FIG. 7) and second embodiment (FIG. 8). In the case of the first embodiment (FIG. 7) the scan pattern shown in FIG. 11 shows the electron or other charged particle beam spot 220 and the optical beam spot 230 overlapping at a fixed coincidence point 190, while the mechanical scanning stage 110 moves the sample to expose each sample pixel area 240 in the region of interest 210 to the illumination by both fixed beams. In the case of the second embodiment (FIG. 8), the scan pattern shown in FIG. 11 shows the electron beam spot 220 and the optical beam spot 230 overlapping at the coincidence point 190, while the coincidence point 190 is scanned to expose each sample pixel area 240 in the region of interest 210 to the illumination by both synchronized beams. One scan line 235 is defined as a continuous scan of pixels in one direction before a change of direction or return to the beginning of the line of pixels is encountered. A raster type scanning pattern in which the scan direction alternates from one line to the next is shown as an example.

Figure 12:
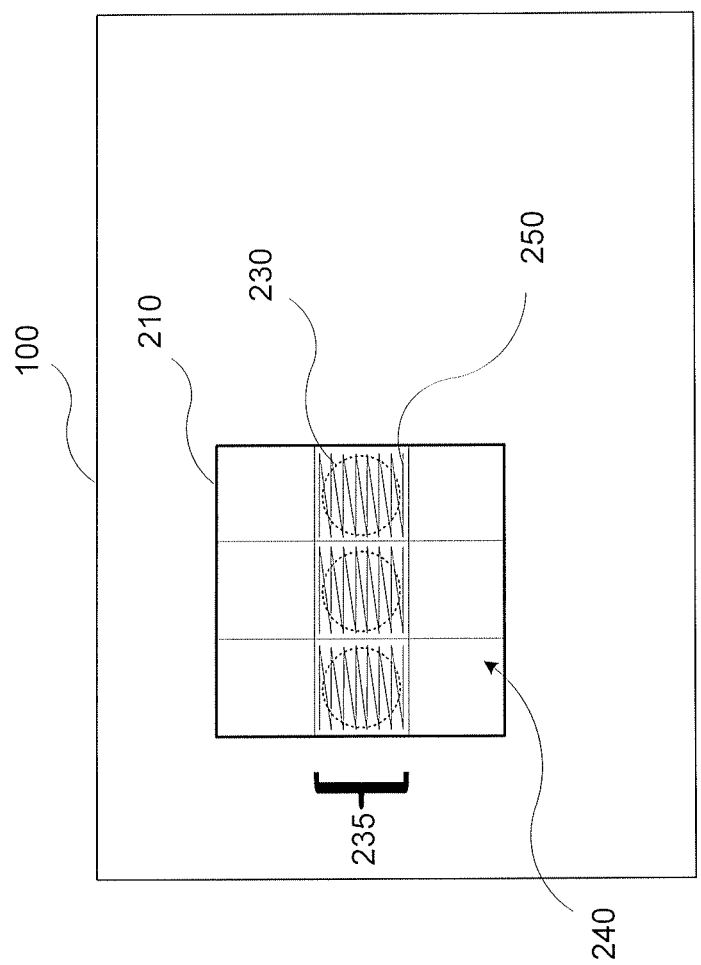
FIG. 12 is a schematic diagram showing a scanning pattern according to another embodiment.

FIG. 12 shows a schematic diagram of a scanning pattern that represents a step in the fourth embodiment (FIG. 10). Again, this is a two-dimensional view of the object plane within sample 100. In the fourth embodiment (FIG. 10), the step of scanning the first imaging beam may further comprises averaging the imaging signal in order to obtain an average signal response from each sample pixel area 240 since the size of each sample pixel area 240 is determined by the optical beam spot 230 and is much larger than the charged particle (e.g., electron) beam spot 220. Alternatively, instead of averaging, the charged particle beam can be scanned using its own subpixel scanning pattern 250 within each sample pixel area 240 area to collect an image corresponding to each sample pixel area 240, as described earlier in connection with FIG. 10. Ultimately the images corresponding to each sample pixel area 240 can be assembled into an image of the entire region of interest 210 providing a spatial resolution appropriate for the charged particle beam spot 220 and a much higher spatial resolution than that achieved by the optical beam spot 230. One scan line 235 is defined as a continuous scan of pixels in one direction before or a change of direction or return to the beginning of the next line of pixels is performed.

Figure 13:
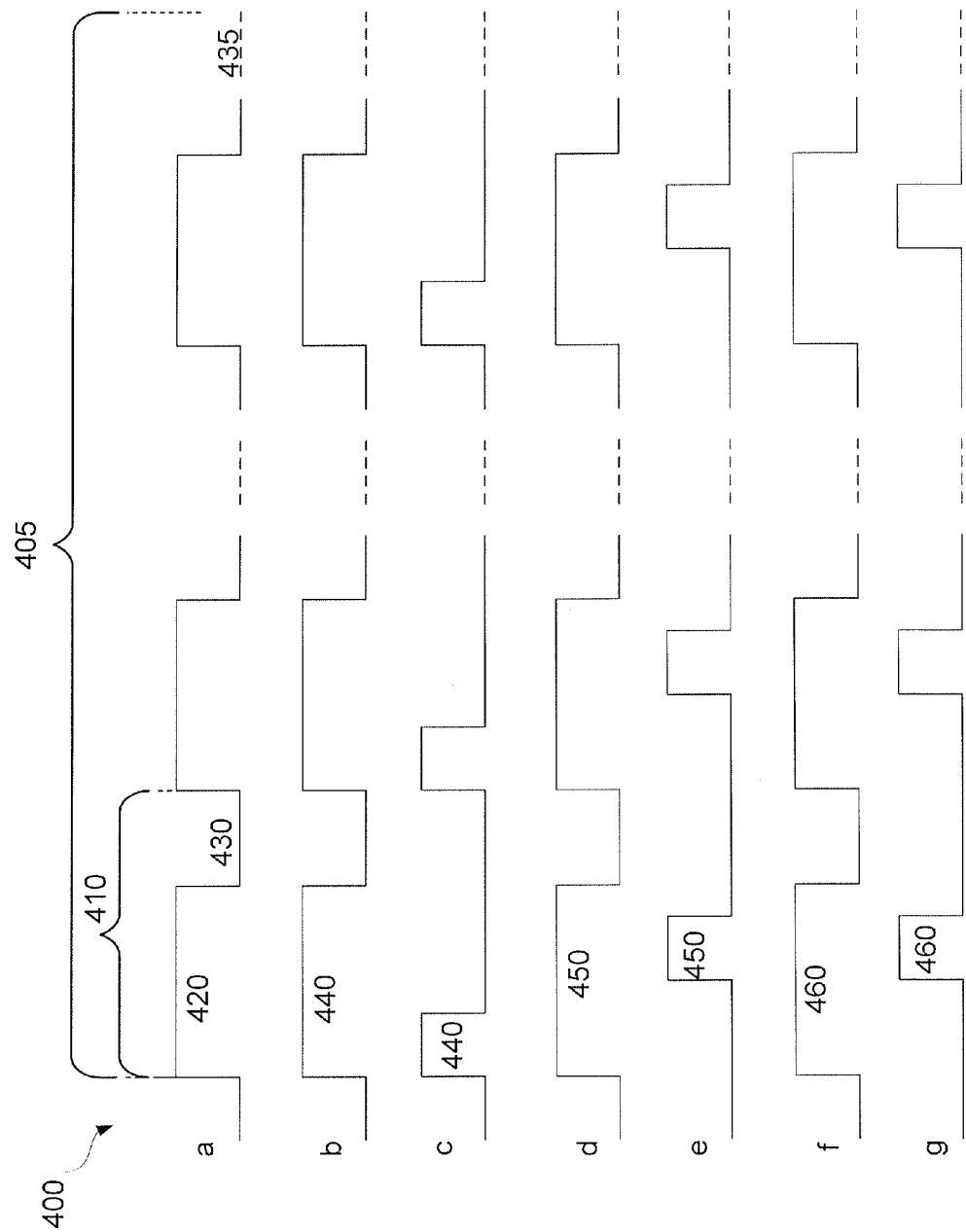
FIG. 13 is a timing diagram showing scanning and data collection according to different embodiments.

Finally, a timing diagram is shown in FIG. 13 illustrating a possible timing pattern 400 containing signals related to the four exemplary embodiments heretofore presented. FIG. 13a shows the time periods associated with data collection and sample or beam motion during the acquisition of image data associated with a line of pixels from an image. FIGS. 13b and 13c show signals associated with acquisition of optical image data, and FIGS. 13d-g depict signals associated with the acquisition of charged particle image data. All patterns are aligned approximately to each other with respect to the horizontal time axis. A signal shown as "high" means that the associated function is being performed for the time during which the graph remains "high."

All signals pertain to a single line during the acquisition of a complete 2D (or multispectral) image. An entire line time (line duration) 405, defined as the total time required to acquire all the pixels along a line covering at least the extent of the region of interest in that scan direction, is shown on each row of the timing diagram. Each line contains signals related to the acquisition of image data for one or more pixels in its associated image, where the time required to acquire a pixel in the image is indicated by the pixel duration 410. During each pixel duration or pixel time 410, data collection may occur during the data collection period 420, and data collection may be paused during the time required to advance the sample or optical beam to the next pixel along the line, defined as pixel-to-pixel motion time 430. To advance scanning from one line in the image acquisition pattern to the next, there may be a line-to-line motion time 435 that is commonly longer than the pixel-to-pixel motion time 430, but which occurs typically only once per line. In FIG. 13a, data collection occurs when the signal is shown high. The pixel-to-pixel motion time 430 may be shorter or longer than the data collection time 420.

Optical data may be collected with an integration or optical data collection time 440. In FIG. 13b, the optical data collection time 440 has approximately the full duration of the overall data collection time 420. But sufficient optical signal levels may allow an optical integration time shorter than the total data collection time, as shown in FIG. 13c.

Charged-particle image data collection, for example for electron beam (e-beam) images from a secondary electron detector, is depicted in FIGS. 13d-g. FIG. 13d shows e-beam data collection 450 occurring for approximately the entire data collection time 420. E-beam data collection 450 may correspond to an integration time for signals from an electron detector, or from any detector generating electronic signals transduced from radiation stimulated by the electron beam incident on the sample, such as x-rays. FIGS. 13d and 13b taken together show both the optical and electron data being collected simultaneously during the entire data collection period 420 of each pixel. This situation might correspond, for example, to the first embodiment using a scanned mechanical stage, or to the second embodiment in which the beams are synchronized and move together. This temporally overlapping data collection works if the signals generated by the two detectors do not interfere with each other or if the stimulating beams do not produce signals in each others' detectors.

FIGS. 13e and 13c apply together for the situation in which such interference between detectors occurs, and the data for the two detectors are preferably taken at different non-overlapping times to avoid this interference. For example, in FIG.

13c, the optical signal integration time 440 can be arranged to occur in the first part of the data collection period 420 (FIG. 13a), and turned off during the electron signal integration time 450 (FIG. 13e) that occurs later in the data collection period 420. Alternatively, the electron signal integration time may be sequenced to occur before optical integration time 440, as long as the two signals do not overlap in time.

FIGS. 13f and 13b taken together illustrate the situation in the fourth embodiment (as described earlier in connection with FIGS. 10 and 12). In this case, the signal 460 is high to indicate scanning (rather than integration or averaging) of the electron beam to make a subpixel electron image. If such scanning interferes with the optical data collection integration time 440 in FIG. 13b, or is interfered with by the optical signals, then subpixel scanning can be arranged to occur in a non-overlapping fashion as shown in FIG. 13g taken together with FIG. 13c. In this example, the subpixel scan time 460 occurs after the optical integration time 440 is complete, but still within the allowable data collection time 420 for each pixel. Subpixel scan time 460 may occur before optical integration time 440 as long as the two functions do not overlap in time, if such overlap would cause interference, as described above.

None of the description in this application should be read as implying that any particular element, step, or function is an essential element which must be included in the claim scope; the scope of patented subject matter is defined only by the allowed claims. Moreover, none of these claims are intended to invoke paragraph six of 35 U.S.C. Section 112 unless the exact words "means for" are used, followed by a gerund. The claims as filed are intended to be as comprehensive as possible, and no subject matter is intentionally relinquished, dedicated, or abandoned.

We claim:

1. A method for acquiring simultaneous and overlapping optical and charged-particle beam images of a sample mounted on a mechanical scanning stage in a multi-beam microscope; the multi-beam microscope having a first imaging beam comprising charged particles having a first focus, a second imaging beam comprising light having a second focus with a spot size that defines a sample pixel area, the method comprising:
   aligning the imaging beams on the sample so that the first focus and the second focus overlap at a coincidence point;
   locating the sample so as to place a selected object plane at the coincidence point;
   specifying a region of interest within the object plane for image acquisition;
   scanning the sample using the mechanical scanning stage to cover the entire region of interest with the imaging beams; and
   recording imaging signals corresponding to the imaging beams while scanning proceeds, whereby the recorded images form pixel-by-pixel simultaneous and overlapping images corresponding to the first and second imaging beams.

2. The method of claim 1, further comprising forming an image set from the pixel-by-pixel simultaneous and overlapping images so that the pixel-by-pixel simultaneous and overlapping images can be viewed side by side.

3. The method of claim 1, further comprising forming an image set from the pixel-by-pixel simultaneous and overlapping images so that the pixel-by-pixel simultaneous and overlapping images are overlaid with control of transparency for each of the pixel-by-pixel simultaneous and overlapping images.

4. The method of claim 3 further comprising forming a single composite overlaid image from the pixel-by-pixel simultaneous and overlapping images.

5. The method of claim 1 further comprising recording at least one spectrum from one or more of the sample pixel areas.

6. A method for acquiring simultaneous and overlapping optical and charged-particle beam images of a sample mounted on a stage in a multi-beam microscope; the multi-beam microscope having a first imaging beam comprising charged particles having a first focus, a second imaging beam comprising light having a second focus with a spot size that defines a sample pixel area, the method comprising:
   aligning the imaging beams on the sample so that the first focus and the second focus overlap at a coincidence point;
   locating the sample so as to place a selected object plane at the coincidence point;
   specifying a region of interest within the object plane for image acquisition;
   scanning the coincidence point of the first and second imaging beams so that the coincidence point remains in the object plane while exposing the entire region of interest to the imaging beams; and
   recording imaging signals corresponding to the imaging beams while scanning proceeds, whereby the recorded images form pixel-by-pixel simultaneous and overlapping images corresponding to the first and second imaging beams.

7. The method of claim 6, further comprising forming an image set from the pixel-by-pixel simultaneous and overlapping images so that the pixel-by-pixel simultaneous and overlapping images can be viewed side by side.

8. The method of claim 6, further comprising forming an image set from the pixel-by-pixel simultaneous and overlapping images so that the pixel-by-pixel simultaneous and overlapping images are overlaid with control of transparency for each of the pixel-by-pixel simultaneous and overlapping images.

9. The method of claim 8 further comprising forming a single composite overlaid image from the pixel-by-pixel simultaneous and overlapping images.

10. The method of claim 6 further comprising recording at least one spectrum from one or more of the sample pixel areas.

11. A method for acquiring simultaneous and overlapping optical and charged-particle beam images of a sample mounted on a stage in a multi-beam microscope; the multi-beam microscope having a first imaging beam comprising charged particles having a first focus, a second imaging beam comprising light having a second focus with a spot size that defines a sample pixel area, the method comprising:
   aligning the imaging beams on the sample so that the first focus and the second focus overlap at a coincidence point;
   locating the sample so as to place a selected object plane at the coincidence point;
   specifying a region of interest within the object plane for image acquisition;
   scanning the first and second imaging beams independently so that the first and second foci remain in the object plane while covering the entire region of interest with the imaging beams; and
   recording imaging signals corresponding to the imaging beams while scanning proceeds, whereby the recorded images form simultaneous and at least partially overlapping images corresponding to the first and second imaging beams.

12. The method of claim 11, further comprising forming an image set from the simultaneous and at least partially overlapping images so that the simultaneous and at least partially overlapping images can be viewed side by side.

13. The method of claim 11 further comprising forming an image set from the pixel-by-pixel simultaneous and overlapping images so that the simultaneous and at least partially overlapping images are overlaid with control of transparency for each of the simultaneous and at least partially overlapping images.

14. The method of claim 13 further comprising forming a single composite overlaid image from the simultaneous and at least partially overlapping images.

15. The method of claim 11 further comprising recording at least one spectrum from one or more of the sample pixel areas.

16. A method for acquiring simultaneous and overlapping optical and charged-particle beam images of a sample mounted on a stage in a multi-beam microscope; the multi-beam microscope having a first imaging beam comprising charged particles having a first focus, a second imaging beam comprising light having a second focus with a spot size that defines a sample pixel area, the method comprising:
　aligning the imaging beams on the sample so that the first focus and the second focus overlap at a coincidence point;
　locating the sample so as to place a selected object plane at the coincidence point;
　specifying a region of interest within the object plane for image acquisition;
　scanning the second focus relative to the sample to cover the entire region of interest with the second imaging beam;
　scanning the first focus independently within each sample pixel area; and
　recording imaging signals corresponding to the imaging beams while scanning proceeds, whereby the recorded images form simultaneous and overlapping images corresponding to the first and second imaging beams.

17. The method of claim 16, wherein the step of scanning the first focus further comprises averaging the imaging signal corresponding to the first imaging beam.

18. The method of claim 16, wherein the step of scanning the first focus further comprises scanning the first imaging beam within each sample pixel area to collect an image corresponding to each sample pixel area.

19. The method of claim 16, wherein the stage is a mechanical scanning stage, and the step of scanning the second focus relative to the sample comprises moving the mechanical scanning stage while the second imaging beam remains stationary.

20. The method of claim 16, wherein the step of scanning the second focus relative to the sample comprises moving the second imaging beam while the stage remains stationary.

21. The method of claim 16, further comprising recording at least one spectrum from one or more of the sample pixel areas.

22. The method of claim 1, where the step of recording imaging signals further compromises gating one or both of the imaging beams in time.

23. The method of claim 6, where the step of recording imaging signals further compromises gating one or both of the imaging beams in time.

24. The method of claim 11, where the step of recording imaging signals further compromises gating one or both of the imaging beams in time.

25. The method of claim 16, where the step of recording imaging signals further compromises gating one or both of the imaging beams in time.

26. A method for acquiring simultaneous and overlapping optical and charged-particle beam images of a sample mounted on a stage in a multi-beam microscope; the multi-beam microscope having a first imaging beam comprising charged particles having a first focus, a second imaging beam comprising light having a second focus with a spot size that defines a sample pixel area, the method comprising:
　aligning the imaging beams on the sample so that the first focus and the second focus overlap at a coincidence point;
　locating the sample so as to place a selected object plane at the coincidence point;
　specifying a region of interest within the object plane for image acquisition;
　scanning the first imaging beam while maintaining the focus of the second imaging beam, so that the first and second foci remain in the object plane while covering the entire region of interest with the imaging beams; and
　recording imaging signals corresponding to the imaging beams while scanning of the first imaging beam proceeds, whereby the recorded images form simultaneous and at least partially overlapping images corresponding to the first and second imaging beams.

27. The method of claim 26, further comprising forming an image set from the simultaneous and at least partially overlapping images so that the simultaneous and at least partially overlapping images can be viewed side by side.

28. The method of claim 26 further comprising forming an image set from the pixel-by-pixel simultaneous and overlapping images so that the simultaneous and at least partially overlapping images are overlaid with control of transparency for each of the simultaneous and at least partially overlapping images.

29. The method of claim 28 further comprising forming a single composite overlaid image from the simultaneous and at least partially overlapping images.

30. The method of claim 26 further comprising recording at least one spectrum from one or more of the sample pixel areas.

\* \* \* \* \*